United States Patent [19]

Liprie

[11] Patent Number: 5,084,002
[45] Date of Patent: Jan. 28, 1992

[54] ULTRA-THIN HIGH DOSE IRIDIUM SOURCE FOR REMOTE AFTERLOADER

[75] Inventor: Samuel F. Liprie, Lake Charles, La.

[73] Assignee: Omnitron International, Inc., Houston, Tex.

[21] Appl. No.: 228,400

[22] Filed: Aug. 4, 1988

[51] Int. Cl.$^5$ .............................................. A61N 5/00
[52] U.S. Cl. ........................................... 600/7; 600/3
[58] Field of Search ............................... 600/1, 2, 3, 7; 128/772; 604/264; 250/506.1; 254/644–645

[56] References Cited

U.S. PATENT DOCUMENTS

| | | |
|---|---|---|
| 1,753,287 | 4/1930 | Failla . |
| 1,954,868 | 4/1934 | Failla et al. ............... 174/177 |
| 2,322,902 | 6/1943 | Wappler ..................... 29/34 |
| 2,429,438 | 10/1947 | Wappler . |
| 2,546,761 | 3/1951 | Loftus ........................ 600/7 |
| 2,798,164 | 7/1957 | Untermyer ................. 250/106 |
| 3,060,924 | 10/1962 | Rush . |
| 3,438,365 | 4/1969 | Packer et al. . |
| 3,485,234 | 12/1969 | Stevens . |
| 3,612,058 | 10/1971 | Ackerman . |
| 3,674,006 | 7/1972 | Holmer ....................... 600/7 |
| 3,749,086 | 7/1973 | Kline et al. . |
| 3,924,632 | 12/1975 | Cook . |
| 4,096,862 | 6/1978 | DeLuca ...................... 600/3 |
| 4,190,461 | 2/1980 | Hedger ....................... 134/1 |
| 4,425,919 | 1/1984 | Alston, Jr. et al. . |
| 4,538,622 | 9/1985 | Samson et al. .............. 128/772 |
| 4,554,929 | 11/1985 | Samson et al. .............. 128/772 |
| 4,584,991 | 4/1986 | Tokita et al. ............... 600/3 |
| 4,815,449 | 3/1989 | Horowitz ..................... 600/7 |
| 4,819,618 | 4/1989 | Liprie ......................... 600/7 |

FOREIGN PATENT DOCUMENTS

857992  1/1961  United Kingdom .

OTHER PUBLICATIONS

Two-Page Document Entitled, "Iridium 192 Wires," Published by Syncor International Corporation.
Four-Page Document Entitled, "Interstitial Accessories", Published by Syncor International Corporation.
Two-Page Document Entitled, "Interstitial Therapy Price List", Published in May, 1984, by Syncor International Corporation.
A One-Page Document Entitled, "MicroSelectron-HDR Iridium Source," Published by Nucletron Corporation.
A Document Entitled, "MicroSelection IDR/MDR 192Ir 127Cs," Published by Nucletron Trading B.V.
A Document Entitled, "Gammamed IIi System Dr. Sauerwein," Published by Mick Radio-Nuclear Instruments, Inc.

*Primary Examiner*—Stephen C. Pellegrino
*Assistant Examiner*—Ralph A. Lewis
*Attorney, Agent, or Firm*—Fitch, Even, Tabin & Flannery

[57] ABSTRACT

An ultra-thin iridium source is used for the treatment of cancerous tissue, particularly in areas of the human body, such as the brain, where minimization of trauma to adjacent tissue is a high priority. The source is formed of a relatively pure iridium seed encapsulated in the end region of a relatively pure unitary platinum delivery wire. The relatively pure iridium source is irradiated to a high activity level (e.g. 10 curie) even though having a short overall length (e.g. 10 millimeter) and ultra-thin diameter (e.g. about ⅛ millimeter). The platinum delivery wire defines a substantially uniform ultra-thin cross section of approximately 0.5 millimeter diameter. The iridium source is formed within the unitary platinum delivery wire without resort to welding or other inherently unreliable attachment systems. Delivery of the high activity pure iridium source to treatment area is achieved using remote afterloader equipment.

14 Claims, 1 Drawing Sheet

ULTRA-THIN HIGH DOSE IRIDIUM SOURCE FOR REMOTE AFTERLOADER

BACKGROUND OF THE INVENTION

The present invention relates to radiation treatment of cancerous tissue internally within the human body. More specifically, the present invention pertains to a high activity/high dose iridium source adapted for remote afterloader implantation in living tissue.

In general the irradiation of tissue as a means to reduce or eliminate malignancy has been known for many years. The specific procedure and equipment required for any given treatment, however, varies according to numerous factors including the location of the cancer within the body, its level of development and spread, and the age and condition of the patient.

For example, Wappler U.S. Pat. Nos. 2,322,902 and 2,439,438 and Packer U.S. Pat. Nos. 3,458,365, relate to the manufacture of radium and xenon gas "seeds" which may be used to treat cancer by physically implanting the seeds at the cancer site in the patient's body. As described in the Packer patent, these implants may be of low dosage, thereby facilitating the permanent implantation thereof as well as permitting safe handling by doctors and other personnel during surgical installation. This form of irradiation treatment is limited to those regions of the body in which placement of the seeds can be effected without undue trauma to adjacent normal tissue.

Another known cancer treatment procedure involves the insertion of a radioactive source through a guide tube, which may be an elongate needle or catheter. The present invention relates generally to this radiation source placement technique.

While the use of a guide tube (needle or catheter) offers relatively safe and easy access to many parts of the body, it is not without its limitations. First, the placement of the guide tube, while less invasive than alternative direct surgical placement, nevertheless can traumatize tissue along its path of insertion. This is particularly true for treatment of, for example, brain tumors, where a hole to receive the guide tube must be drilled through the cranium and brain tissue. Any drilling of brain tissue causes irreparable damage thereto and consequently such drilling is desirably kept to a minimum.

Second, for low intensity radiation treatments, the source of radiation must remain resident for extended periods of time, often in excess of several days. As the patient will not normally be hospitalized during this entire extended treatment cycle, the guide tubes must be inserted, positioned, and terminated such that the patient may undertake much of his normal daily routine.

Known indirect guide tube products typically employ an iridium/platinum alloy of approximately 30% iridium. These products are often used in connection with low intensity, source-resident type procedures, that is, where the source remains in the body for extended durations. Known iridium alloy sources used for such irradiation generally exhibit activity levels between about 0.5 and 25 millicurie/centimeter. (The overall activity level thus varies as a function of the length of the active region, which may be several centimeters.)

Alternatively, iridium/platinum alloy sources of proportionately larger diameter have been fabricated to achieve the higher radiation activity levels necessary for short term treatment procedures. As noted, placement of these larger diameter sources results in correspondingly increased damage to normal tissue.

The smallest source assemblies heretofore used have been about 1 millimeter in diameter.

Furthermore, known guide tube sources are fabricated by welding or otherwise affixing an iridium alloy source to the end of a steel "fish" or delivery wire. Insertion of these relatively large sources can be frustrated where the guide tube has been oriented, for medical reasons, along a curved contour. In fact, stresses induced during source insertion have been known to break the source from the delivery wire at its point of welded attachment. This breakage problem is particularly acute where it is expected that the iridium source will be reused for a number of surgical procedures. Repeated flexure ultimately causes joint fatigue and failure.

Radioactive iridium is a common source of irradiation for cancer treatment because it has a convenient half life and emits gamma rays of suitable energy. The useful isotope is iridium 192, which has a half life of about 74 days. This is sufficiently long to permit use of the source at some time and distance from its creation. It emits gamma rays of a number of useful energies in the range of hundreds of KeV and less than about 0.5 MeV. One such gamma ray energy is about 484 KeV. This is energetic enough to pass out of the guide tube and through adjacent tissue to irradiate the tumor but is not so energetic as to reach more remote parts of the body to the detriment thereof. That is, the radiation can be relatively concentrated at the tumor without destroying too much healthy tissue.

A problem with certain prior art iridium guide tube sources has been attributed to their fabrication. Iridium 192 is produced by the irradiation of iridium 191 in a nuclear reactor. At least partly because of their size and shape, the sources were assembled with respective delivery wires before irradiation, which resulted in the irradiation of these wires, rendering them radioactive as well, with undesirable half lives and energies.

SUMMARY OF THE INVENTION

The present ultra-thin iridium guide tube source overcomes many of the above limitations by utilizing a high activity iridium core member secured within the end of a substantially nonradioactive delivery wire.

In accordance with the present invention, the radioactive core member is made by irradiating a natural iridium member with thermal neutrons in a nuclear reactor. Natural iridium is 33% iridium 191 and 67% iridium 193. Iridium 191 has a substantial thermal neutron cross section and captures thermal neutrons with a substantial probability to form iridium 192, which is radioactive with a half-life of 74 days. Iridium 193 has a lesser thermal neutron cross section and, hence, is not so readily made radioactive. Further, the iridium 194 that is formed has a half-life that is very short relative to that of iridium 192 and, hence, rapidly decays within a time short relative to the half-life of iridium 192 to a negligible level relative to the remaining iridium 192.

The present invention also contemplates a more concentrated source in order that high radioactivity may be provided in a smaller diameter. To this end the core member is made of relatively pure iridium rather than the 30% iridium/platinum of the prior art. By relatively pure iridium is meant a purity of at least about 90%, where the remainder is material that following the neutron irradiation becomes negligibly radioactive relative to the iridium 192 within a time after neutron irradiation short relative to the half life of iridium 192. Negligibly radioactive means that the energies of the radiation are negligibly small relative to the radiation from iridium 192 and the rate of disintegration is negligibly small relative to the disintegration of iridium 192. The relatively pure iridium core is activated in a thermal neutron flux to a desired activity, which may be at least 10 curies. This permits a full radiation treatment of a few minutes duration with a thin guide tube. The magnitude of the activating thermal neutron flux is not critical; however, it should be sufficient to achieve the desired degree of radioactivity well within the half-life of iridium 192 lest the iridium 192 decay almost as fast as it is formed, resulting in costly wasteful neutron flux. A time of a few weeks has proven practical.

The core member is fabricated by encapsulating it in the end of a unitary delivery wire prior to neutron irradiation. As the delivery wire is then itself irradiated by neutrons, it is essential that it be made of material that is negligibly radioactive relative to the iridium 192 within a time after neutron irradiation that is short relative to the half-life of iridium 192. This may be material that has a thermal neutron capture cross section negligible relative to that of iridium 191, so as not to become very radioactive in the first place. It may be material that becomes radioactive with a half-life so short relative to that of iridium 192 that any radioactivity substantially decays away while leaving iridium 192. It may be material that provides radiation of such low energy relative to the radiation from iridium 192 as to have substantially no penetration and, hence, substantially no physiological effect. It may be material with all these properties. In addition it must have the necessary structural qualities as to permit driving the core member through the guide tube and protecting it from abrasion or breakage, assuring the integrity of the source so that no parts thereof are left in a patient's body. In accordance with the present invention, platinum has proven to have suitable properties.

The core and delivery wire assembly made in accordance with the present invention can be and is made of smaller diameter than has previously been achieved successfully, that is, substantially smaller than 1 millimeter in diameter, preferably less than about 0.7 millimeters, with the core member suitably smaller, preferably less than about 0.2 millimeters. An assembly of about 0.5 millimeters in diameter has proven practical in reaching tumors in previously inaccessible regions, such as behind the eye. In such an assembly the core member was about 0.125 millimeters in diameter. Such fine assemblies may be formed by inserting a larger diameter core member in a uniform larger diameter platinum wire along its axis and drawing the assembly down to the desired diameter.

There are no welds or other junctions of unpredictable quality to break when urging the present ultra-narrow source through tight radius curves. The narrow diameter of the present delivery wire, in addition to its suitability for minimum tissue damage ultra-fine guide tube insertion, is more flexible and therefore better adapted for treatment procedures requiring a convoluted catheter routing.

These and other aspects and advantages of the invention will be further apparent from the following detailed description, particularly when taken in conjunction with the accompanying drawings.

DESCRIPTION OF THE PREFERRED EMBODIMENT

Figures 1, 2:
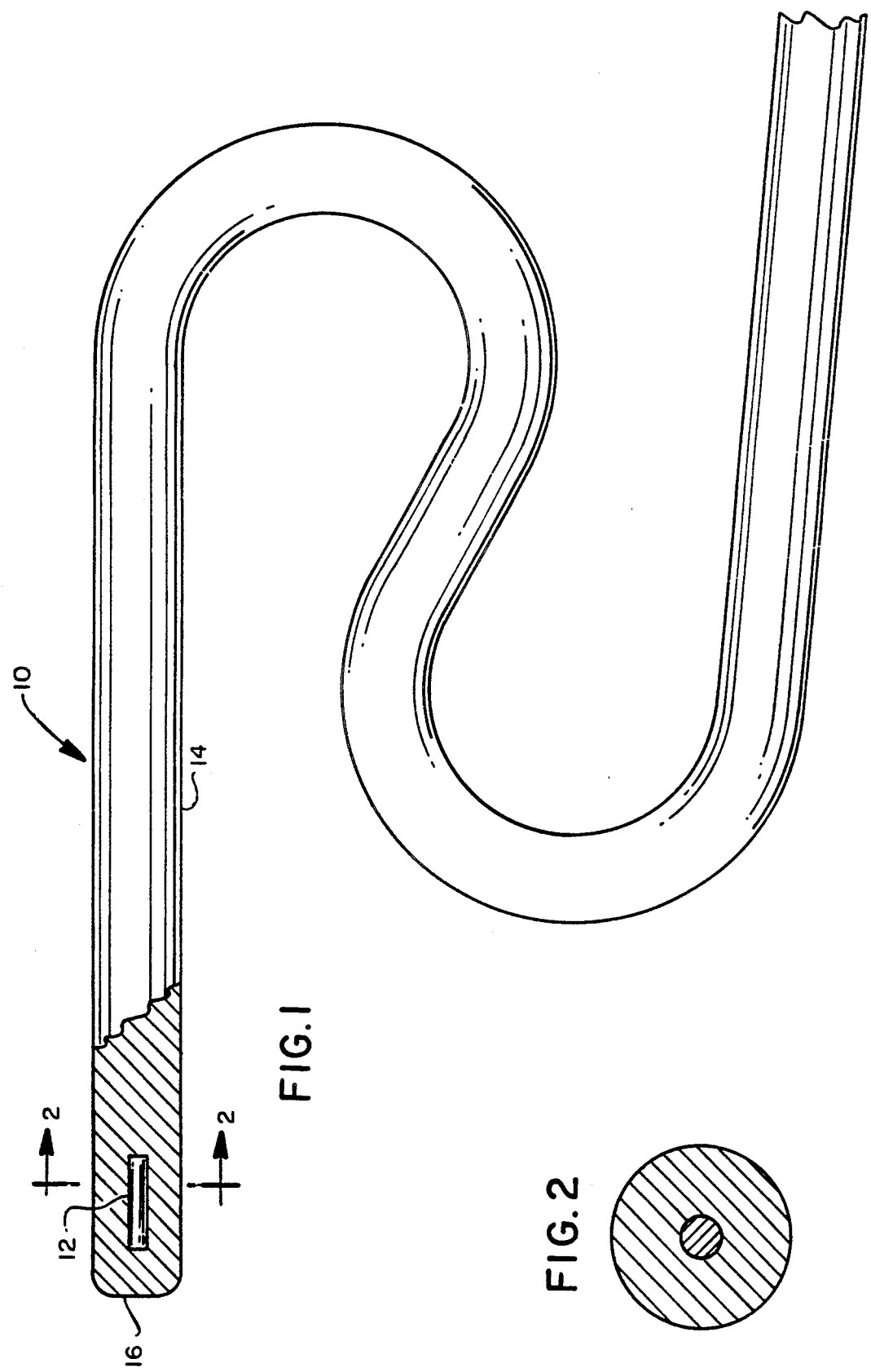
FIG. 1 is a side elevation view of an iridium/platinum source assembly according to the present invention with portions shown in axial cross section to reveal details of iridium core placement in a platinum wire; and, FIG. 2 is an enlarged transaxial sectional view of the source shown in FIG. 1 taken substantially along line 2—2 of FIG. 1.

FIG. 1 illustrates the high dose iridium/platinum radioactive cancer treatment source 10 of the present invention. Source 10 includes a relatively pure iridium core member or seed 12 formed, as discussed in more detail below, in the end of a unitary elongate relatively pure platinum delivery wire 14.

Iridium enhancement is not required. Natural iridium, comprising the isotopes of atomic weight 191 and 193, may be used. Natural iridium is approximately one-third iridium 191, which is activated in a nucleaar reactor by thermal neutron flux to iridium 192, which has a principal energy level of 484 KeV and a half-life of 74 days.

Fabrication of the core member 12 using relatively pure iridium advantageously permits activation of the source to a high dose level while simultaneously maintaining the core 12 and delivery wire 14 at the smallest possible diameter, thereby minimizing tissue damage caused by guide tube or catheter placement.

As used herein, high dose signifies an activity level on the order of 10 curies. A 10 curie source is suitable for rapid, nonresident treatment sessions generally in the order of from one to ten minutes. For example, a 10 curie iridium 192 source (at 484 KeV) will provide a 3000 rad dose in ten minutes. Such a dose may be divided into four sessions to minimize the adverse effects of an unduly rapid treatment profile. In any event, radiation treatments are preferably effected by the temporary and short duration placement of the requisite guide tubes within the patient as contrasted with the long-term, multiple day treatment process of alternative low dose techniques.

The iridium core 12 is activated by placing the entire source 10, including the unitary delivery wire 14, within a thermal neutron flux field. Flux field residence required for a desired activation level depends upon the neutron flux density and the purity and mass of the iridium core. A shorter residence is required upon use of the preferred relatively pure iridium source.

By far the greatest expense associated with a high activity radioactive source is the cost of neutron flux activation. As this expense is directly proportional to the residence or exposure time of the iridium source to the neutron flux field, substantial cost benefits accrue by using a concentrated relatively pure iridium source with its correspondingly lower irradiation residence time requirement to achieve the desired activation After activation the source 10 must be maintained in a shielded enclosure or "safe" when not in use. Due to its high activity level, the source cannot safely be handled by doctors or other personnel, and, therefore, patient treatment is achieved by linking the guide tubes or catheters to a remotely actuated apparatus commonly known as an afterloader (not shown). The afterloader serves to reposition the source remotely from the safe to the site of treatment within the patient and, thereafter, to withdraw and replace the source in the safe.

Referring again to FIG. 1, a relatively pure iridium core suitable for a 10 curie activation intensity can advantageously be formed of narrow diameter and of suitable overall length. Specifically, the iridium core 12 is preferably about 0.125 millimeters in diameter and about 10 millimeters in length. A longer iridium core, e.g., 20 millimeters, would advantageously reduce the number of discrete positions or steps required for any given treatment session. Iridium cores in excess of one centimeter, however, encounter manufacturing limitations. Further it is often desirable to more nearly approximate a point source, although at least about 5 millimeters is preferred.

The iridium core 12 is fabricated in the end of a platinum delivery wire 14, preferably spaced inwardly about 1 millimeter from the distal end 16 thereof. Platinum is preferred by reason of its mechanical strength and flexibility as well as its relatively short radioactive half-life upon thermal neutron irradiation (about 14 days), and its relatively low thermal neutron capture cross section. Unlike the prior art stainless steel delivery wires, platinum wire, when exposed to thermal neutron flux, is substantially nonradioactive relative to the irradiated iridium in a time short relative to the half-life of iridium 192. The wire is made of relatively pure platinum in the sense that any other elements present do not weaken the structural properties of the platinum and when exposed to thermal neutron flux are substantially nonradioactive relative to irradiated iridiation in a time short relative to the half-life of iridium 192.

The platinum delivery wire may be of any convenient length consistent with the surgical procedures contemplated and with the requirements of the remote afterloader equipment with which the iridium source is intended to be used. A typical length is 2.1 meters.

As previously noted, one of the principal objectives of the present invention is to provide a high dose iridium source of the smallest possible diameter In this connection, the platinum wire 14 of the present source is made less than 1 millimeter and preferably about 0.5 millimeter in diameter. Although delivery wires of narrower diameter are contemplated, the present 0.5 millimeter system represents a practical lower dimensional limit in view of present manufacturing technology.

The source assembly 10 may be fabricated by conventional mechanical or laser drilling techniques whereby a hole to receive the iridium core 12 is drilled in the distal end of the platinum wire 14. However, in view of the extremely small diameter of the present source and, further, the difficulty in working with pure iridium, it is preferred to fabricate the present source by a drawing process whereby the iridium is disposed in a larger platinum wire and drawn to the desired smaller diameter.

It will be appreciated that the above described source 10 provides for the rapid nonresident treatment of cancerous tissue through the incorporation of a physically small, high activity pure iridium source into a platinum delivery wire of correspondingly narrow diameter. In this manner, access to and treatment of cancer tissue in remote and sensitive regions of the body may be effected through the use of extremely fine needles, or catheters or other guide tubes with a minimum of damage to surrounding normal tissue. It will be further appreciated that the present source is integral, that is, a unitary delivery wire 14 is formed over the active iridium element 12 without resort to welds or other bonding systems. This, in turn, allows for routing of the source through irregular and tightly contoured catheters with substantially less danger of source separation, separation which is known to occur in conventional systems at welded junctions between the delivery wire and the active radiation source.

What is claimed is:

1. A high activity, ultra-thin radiation source assembly for the nonresident treatment of cancerous tissue within a living body with minimum damage to surrounding normal tissue and for insertion into the living body through an ultra-thin guide tube by a remote controlled afterloader apparatus, comprising:
   an elongate unitary delivery wire having a treatment end; and
   an iridium core member encapsulated within the treatment end of the said elongate unitary delivery wire, said iridium core member being radioactive from irradiation of the assembled elongate unitary delivery wire and iridium core member by thermal neutrons, the materials of said iridium core member and elongate unitary delivery wire other than iridium being substantially nonradioactive relative to the activity of iridium 192 in said iridium core member within a time after said irradiation short relative to the half-life of iridium 192.

2. A high activity, ultra-thin radiation source assembly according to claim 1 wherein said iridium core member consists of relatively pure iridium and said elongate unitary delivery wire consists of relatively pure platinum.

3. A high activity, ultra-thin radiation source assembly for the nonresident treatment of cancerous tissue within a living body with minimum damage to surrounding normal tissue and for insertion into the living body through an ultra-thin guide tube by a remote controlled afterloader apparatus, comprising:
   an elongate unitary delivery wire having a treatment end, said elongate unitary delivery wire being round and substantially less than one millimeter in diameter at the treatment end; and
   an iridium core member encapsulated within the treatment end of the said elongate unitary delivery wire, said iridium core member being radioactive from irradiation of the assembled elongate unitary delivery wire and said iridium core member by thermal neutrons, the materials of said iridium core member and elongate unitary delivery wire other than iridium being substantially nonradioactive relative to the activity of iridium 192 in said iridium core member within a time after said irradiation short relative to the half-life of iridium 192.

4. A high activity, ultra-thin radiation source assembly according to claim 3 wherein said elongate unitary delivery wire is about 0.5 millimeters in diameter at least at the treatment end.

5. A high activity, ultra-thin radiation source assembly according to claim 3, wherein said iridium core member is no longer than about 10 millimeters and is activated to at least about 10 curies.

6. A high activity, ultra-thin radiation source assembly for the nonresident treatment of cancerous tissue within a living body with minimum damage to surrounding normal tissue and for insertion into the living body through an ultra-thin guide tube by a remote controlled afterloader apparatus, comprising:

an elongate unitary delivery wire having a treatment end; and a relatively pure iridium core member encapsulated within the treatment end of the said elongate unitary delivery wire, said relatively pure iridium core member being radioactive from irradiation of the assembled elongate unitary delivery wire and relatively pure iridium core member by thermal neutrons, the materials of said relatively pure iridium core member and elongate unitary delivery wire other than iridium being substantially nonradioactive relative to the activity of iridium 192 in said iridium core member within a time after said irradiation short relative to the half-life of iridium 192.

7. A high activity, ultra-thin radiation source assembly according to claim 6 wherein said elongate unitary delivery wire is about 0.5 millimeters in diameter at least at the treatment end.

8. A high activity, ultra-thin radiation source assembly according to claim 6 wherein said relatively pure iridium core member is no longer than about 10 millimeters and is activated to at least about 10 curies.

9. A high activity, ultra-thin radiation source assembly for the nonresident treatment of cancerous tissue within a living body with minimum damage to surrounding normal tissue and for insertion into the living body through an ultra-thin guide tube by a remote controlled afterloader apparatus, comprising:

a relatively pure platinum elongate unitary delivery wire having a treatment end; and an iridium core member encapsulated within the treatment end of said relatively pure platinum elongate unitary delivery wire, said iridium core member being radioactive from irradiation of the assembled relatively pure platinum elongate unitary delivery wire and iridium core member by thermal neutrons, the materials of said iridium core member and relatively pure platinum elongate unitary delivery wire other than iridium being substantially nonradioactive relative to the activity of iridium 192 in said iridium core member within a time after said irradiation short relative to the half-life of iridium 192.

10. A high activity, ultra-thin radiation source assembly according to claim 9 wherein said relatively pure platinum elongate unitary delivery wire is about 0.5 millimeters in diameter at least at the treatment end.

11. A high activity, ultra-thin radiation source assembly according to claim 9 wherein said iridium core member is no longer than about 10 millimeters and is activated to at least about 10 curies.

12. A high activity, ultra-thin radiation source assembly for the nonresident treatment of cancerous tissue within a living body with minimum damage to surrounding normal tissue and for insertion into the living body through an ultra-thin guide tube by a remote controlled afterloader apparatus, comprising:

a relatively pure platinum elongate unitary delivery wire having a treatment end, said relatively pure platinum elongate unitary delivery wire being round and substantially less than one millimeter in diameter at the treatment end; and a relatively pure iridium core member encapsulated within the treatment end of the said relatively pure platinum elongate unitary delivery wire, said relatively pure iridium core member being radioactive from irradiation of the assembled relatively pure platinum elongate unitary delivery wire and said relatively pure iridium core member by thermal neutrons, the materials of said relatively pure iridium core member and relatively pure platinum elongate unitary delivery wire other than iridium being substantially nonradioactive relative to the activity of iridium 192 in said relatively pure iridium core member within a time after said irradiation short relative to the half-life of iridium 192.

13. A high activity, ultra-thin radiation source assembly according to claim 12 wherein said relatively pure platinum elongate unitary delivery wire is about 0.5 millimeters in diameter at least at the treatment end.

14. A high activity, ultra-thin radiation source assembly according to claim 12 wherein said relatively pure iridium core member is no longer than about 10 millimeters and is activated to at least about 10 curies.

* * * * *

UNITED STATES PATENT AND TRADEMARK OFFICE
CERTIFICATE OF CORRECTION

PATENT NO. : 5,084,002
DATED : January 28, 1992
INVENTOR(S) : Samuel F. Liprie

It is certified that error appears in the above-indentified patent and that said Letters Patent is hereby corrected as shown below:

On the title page, Under Other Publications, "192Ir 127Cs" should be —192Ir 137Cs—.

On the title page, In the Abstract, line 9, "millimeter" should be —millimeters—.

Column 1, line 19, "Nos." should be —No.—
Column 3, line 4, "half life" should be —half-life—
Column 4, line 5, "elevation" should be —elevational—
         line 25, "nucleaar" should be —nuclear—
Column 5, line 32, "iridiation" should be —iridium—
         line 41, after "diameter" insert —.—

Signed and Sealed this

Twenty-third Day of November, 1993

Attest:

BRUCE LEHMAN

Attesting Officer     Commissioner of Patents and Trademarks